United States Patent [19]

Strawn

[11] Patent Number: Plant 5,329

[45] Date of Patent: Nov. 13, 1984

[54] MINIATURE ROSE PLANT

[76] Inventor: Leslie E. Strawn, 10422 Morningside Ave., Garden Grove, Calif. 92643

[21] Appl. No.: 473,582

[22] Filed: Mar. 9, 1983

[51] Int. Cl.[3] ..... A01H 5/00
[52] U.S. Cl. ..... Plt./8
[58] Field of Search ..... Plt./8

*Primary Examiner*—Robert E. Bagwill

[57] ABSTRACT

The subject of the present disclosure is a new and distinct variety of miniature rose plant characterized by deep clear yellow buds and flowers of distinctive form and further indentified by the erect, dwarf, compact plant.

1 Drawing Figure

1

The present invention relates to a new and distinct variety of hardy, dwarf, bush type rose plant of the miniature class; the variety being primarily characterized — as to novelty — by the deep clear yellow buds and flowers which in general effect are similar to Rise and Shine (U.S. Plant Pat. No. 4,231)

The variety is further characterized by:

The unique buds and flowers.

An abundance of bloom, with flowers borne one to a stem. No side buds.

Slight fragrance.

A plant which is vigorous, of upright growth habit with semi-glossy foliage with pointed leaflets; the buds and flowers being similar in form and size to the pollen parent, Over the Rainbow (Miniature — U.S. Plant Pat. No. 3,472).

The plant, which has a normal height of 10 inches (25 cm), can easily be maintained at this height, or a lesser height, by occasional trimming.

A plant which grows and blooms satisfactorily both in a greenhouse or outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between Sunblest (Hybrid Tea — non patented) as the seed parent and Over the Rainbow (Miniature — U.S. Plant Pat. No. 3,472) as the pollen parent.

Subsequent to origination of the variety I successfully asexually reproduced it in my garden, located as foresaid, (also propagated by Pixie Treasures Rose Nursery, 4121 Prospect Ave., Yorba Linda, Orange County, Calif.) by budding as well as by cuttings; the reproductions having run true in all respects.

The color photograph Illustrates the variety, including the foliage, buds and flowers.

Referring now specifically to the new and distinct variety of miniature rose plant, the following is a detailed description thereof in outline; all major color plate indentifications being by reference to the British Colour Council Horticultural Colour Chart, except where common terms of color definition are employed.

Type: Hardy; dwarf; bushy; upright; seedling; greenhouse; outdoors; cut flowers; garden decoration; pot plant.

Class: Miniature. Variety name: Tiger Butter.

Flowers borne: Singly on upright slender stems.

2

Quantity of bloom: Abundant, both outdoors and in the greenhouse.

Bud:

*Peduncle.*—Medium length, 2 to 3 cm; slender and sturdy; erect; normally straight; light green to medium green; Hairs — covered — microscopic; few glands if any.

*Before calyx breaks.*—Size — small — 2 cm length, may vary. Form — pointed; foliaceous parts usually do not extend beyond the tip of bud. Color — light green with reddish brown line through center of sepals.

*As calyx breaks.*—Color of outside petals showing near Canary Yellow 2/2. Opening — opens well in all weather; unfurls slowly.

Bloom:

*Size when fully open.*—Small, averaging about 4 cm.

*Petalage.*—Double — averaging about 20 to 25 petals, arranged symmetrically, with few petaloids.

*Form.*—Pointed with ovoid shape; as petals unfurl symmetrically the flower retains its form; outside petals curl downward at tip and side edges.

Petals: Moderately thick and of good substance; smooth and satiny on both surfaces.

*Shape.*—Outside petals — broad; round with a pointed tip and a pointed base. Intermediate petals — same as outside petals, slightly smaller, pointed base. Inside petals — same as intermediate petals, not as broad, pointed base. Petaloids — several close to stamens.

Color: One half to three quarters open flower from a plant grown outdoors at Pixie Treasures Rose Nursery, Yorba Linda, Calif., October 1982. All colors stated are close to or near the following color definitions.

*Outside petal.*—Outside surface: Outer edge — Aureolin Yellow 3/2. Center area — Aureolin Yellow 3/1. Base — very pale yellow green. (In very cool weather the outside petals may be streaked in a few places with a light rose pink.) Inside surface: Outer edge — Aureolin Yellow 3/2. Center area — Aureolin Yellow 3/1. Base — same as center area.

*Intermediate petal.*—Outside surface: Outer edge — Lemon Yellow 4/2. Center area — Lemon Yellow 4/1. Base — same as center area. Inside surface: Outer edge — Lemon Yellow 4/2. Center area — Lemon Yellow 4/1. Base — same as center area.

*Inner petal.*—Same as intermediate petal.

General color effect:

*Newly open flowers.*—Symmetrical arrangement of deep clear yellow petals in the tones and tints of Aureolin Yellow and Lemon Yellow; the deeper tones being in the center of the flowers belending to lighter tones toward the outside.

*Three days open.*—Holds same coloring — non fading.

Behavior: Opens well in all weather. Petals of open flowers tend to hang on for 7 to 8 days, becoming slightly lighter from weather and sunlight; then petals fall and calyx remains and forms (usually) a seed hip. Flower longivity (October 1982) — plant in pot — 5 to 6 days; plant in ground — 6 to 7 days. Cut flowers at living room temperature 4 to 5 days or longer.

Reproductive organs:

*Stamens.*—Vary 50 to 60.

*Filaments.*—Light yellow, even lengths — 4 mm.

*Anthers.*—Yellow — orange, introse.

*Pollen.*—Abundant.

*Pistils.*—Project above disc.

*Styles.*—Pale green, several, bunched, 3 mm.

*Ovaries.*—Enclosed in calyx.

*Hips.*—Form readily.

*Sepals.*—Spear shaped, reflexed.

*Seeds.*—Self pollinates readily, 5 or 6 seeds (usually).

Foliage:

*Leaves.*—Compound of five leaflets; 5 to 6 cm in length; moderate substance; semi-glossy.

*Leaflets.*—Broad lanceolate shape; pointed apex; not supported by a petiolule.

Rachis.—Length 3 to 3½ cm; upper side grooved; underside 2 or 3 minute thorns.

*Stipules.*—Short with slender pointed auricles flairing outward at approx. 45 degrees.

*Color.*—Medium to deep green, rachis and serrated edges usually the same green.

Growth:

*Habit.*—Dwarf; upright; height 25 to 30 cm (10 to 12 inches).

*Growth.*—Vigorous; internodes — 12 to 18 mm length between; much branched

*Canes.*—Slender; sturdy.

*Main stems.*—Medium green.

*Branches.*—Medium green; older branches usually stay green.

*Thorns.*—Dilated at base; varying sizes; usually at 90 degrees to stems; small and only moderate amount.

*New shoots.*—Light green edged bronze.

The miniature rose plant and its flowers as herein described may vary in slight detail due to climatic, soil and cultural conditions under which the variety may be grown.

The following is claimed:

1. A new and distinct variety of miniature rose plant of hardy, dwarf, bushy, upright, much branched habit, substantially as illustrated and described, characterized by buds and flowers which are in a color hue similar to Rise and Shine (miniature — U.S. Plant Pat. No. 4,231) giving a coloring effect ot tints and tones of a deep clear yellow and resembling Over the Rainbow (miniature — U.S. Plant Pat. No. 3,472) in form and size, having buds and flowers of a distinct and unusual appearance as compared to other miniature rose plants; said flowers being fully double, uniquely formed with high centers; and further charactized by its vigor, abundant foliage and ease of propagation from soft wood cuttings and by budding, and with an abundance of flowers.

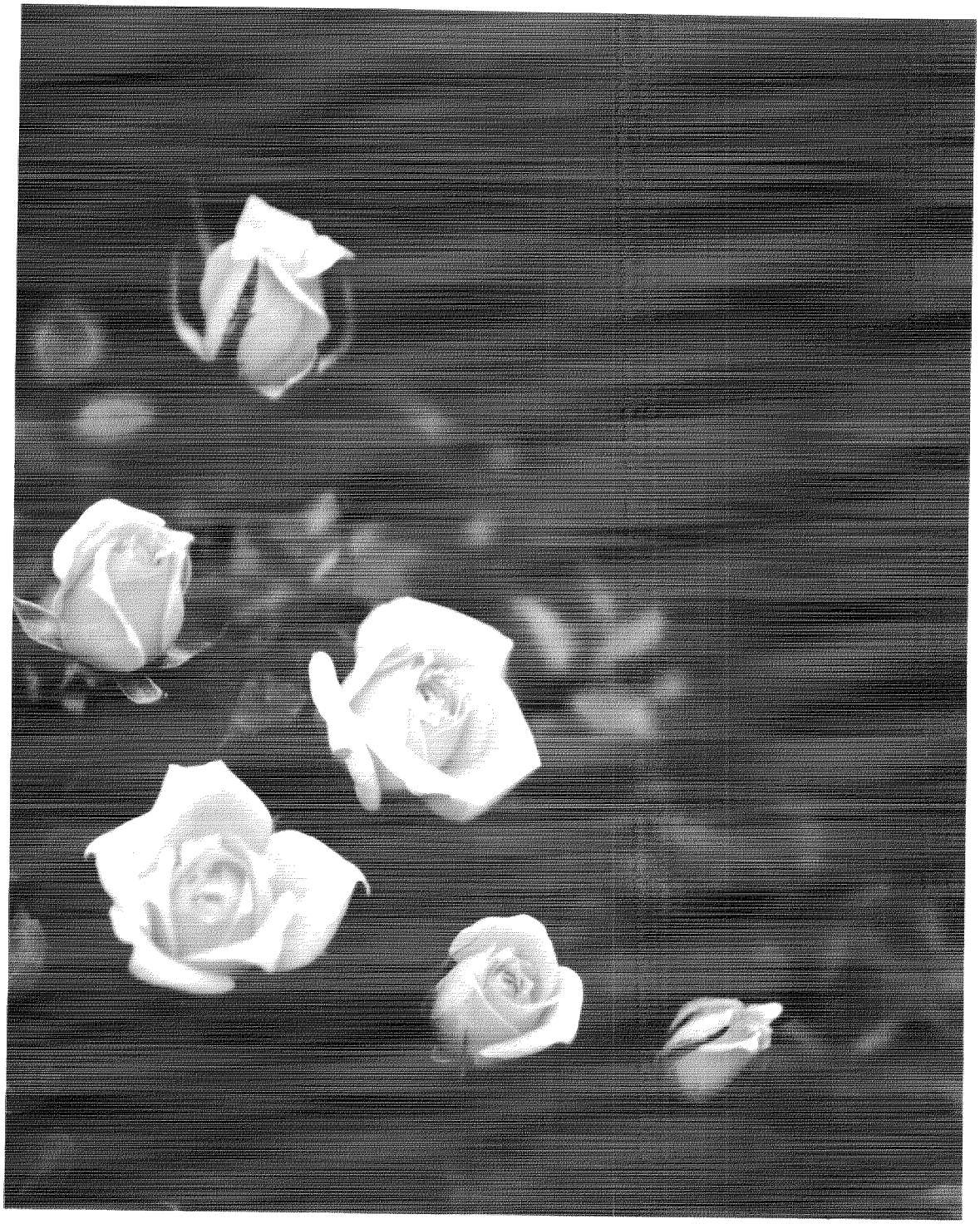

* * * * *